(12) United States Patent
Rucker

(10) Patent No.: US 7,451,096 B2
(45) Date of Patent: Nov. 11, 2008

(54) SYSTEM AND METHOD FOR MANAGING HEALTHCARE COMMUNICATION

(75) Inventor: Donald W. Rucker, Philadelphia, PA (US)

(73) Assignee: Siemens Medical Solution USA, Inc., Malvern, PA (US)

( * ) Notice: Subject to any disclaimer, the term of this patent is extended or adjusted under 35 U.S.C. 154(b) by 1115 days.

(21) Appl. No.: 10/118,494

(22) Filed: Apr. 8, 2002

(65) Prior Publication Data

US 2003/0125987 A1 Jul. 3, 2003

Related U.S. Application Data

(60) Provisional application No. 60/344,127, filed on Dec. 28, 2001.

(51) Int. Cl.
*G06F 19/00* (2006.01)

(52) U.S. Cl. .............................................. 705/3; 705/2

(58) Field of Classification Search .................... 705/2, 705/3
See application file for complete search history.

(56) References Cited

U.S. PATENT DOCUMENTS

| | | | | |
|---|---|---|---|---|
| 5,153,905 | A * | 10/1992 | Bergeron et al. .......... 379/88.23 |
| 5,291,399 | A | 3/1994 | Chaco ........................ 364/413 |
| 5,465,082 | A | 11/1995 | Chaco .................... 340/825.54 |
| 5,721,913 | A * | 2/1998 | Ackroff et al. .......... 707/103 R |
| 5,822,544 | A | 10/1998 | Chaco et al. ................. 395/202 |
| 5,852,408 | A * | 12/1998 | Christiansen et al. .. 340/870.09 |
| 5,867,821 | A | 2/1999 | Ballantyne et al. ............. 705/2 |
| 5,877,675 | A | 3/1999 | Rebstock et al. ........ 340/286.07 |
| 5,899,998 | A | 5/1999 | McGauley et al. ........... 707/104 |
| 5,924,074 | A | 7/1999 | Evans ............................. 705/3 |
| 6,101,481 | A * | 8/2000 | Miller ............................ 705/9 |
| 6,139,494 | A | 10/2000 | Cairnes ....................... 600/300 |
| 6,263,330 | B1 | 7/2001 | Bessette ......................... 707/4 |
| 6,292,783 | B1 | 9/2001 | Rohler et al. ................... 705/2 |
| 6,345,260 | B1 | 2/2002 | Cummings, Jr. et al. ........ 705/8 |
| 2001/0039504 | A1 * | 11/2001 | Linberg et al. .................. 705/3 |
| 2001/0041992 | A1 | 11/2001 | Lewis et al. .................... 705/3 |
| 2002/0019749 | A1 * | 2/2002 | Becker et al. ................... 705/2 |
| 2002/0062230 | A1 * | 5/2002 | Morag et al. .................... 705/3 |
| 2002/0065686 | A1 * | 5/2002 | Monteleone et al. ........... 705/3 |
| 2002/0124028 | A1 * | 9/2002 | Kroeger ...................... 707/530 |
| 2002/0138302 | A1 * | 9/2002 | Bodnick ......................... 705/2 |
| 2002/0188179 | A1 * | 12/2002 | Bulat .......................... 600/300 |
| 2003/0028482 | A1 * | 2/2003 | Burak et al. .................. 705/40 |
| 2003/0036927 | A1 * | 2/2003 | Bowen .......................... 705/4 |

* cited by examiner

*Primary Examiner*—C Luke Gilligan
*Assistant Examiner*—Lena Najarian

(57) ABSTRACT

A system and method for managing healthcare communication. In general, a system according to the present invention comprises a tool, which is integrated with a clinical information system, comprising an engine for dynamically generating and updating lists of patient-specific and provider-specific contact information using data that is accessed from one or more sources via search engine. The lists of contact information are readily accessible by healthcare providers while treating patients using any one of devices. The tool is preferably integrated with a call management system for tracking and flagging clinically necessary telephone calls, for example, that need to be repeated. Furthermore, the tool is preferably integrated with a workflow system to provide dynamic task assignment wherein the lists of contact information are dynamically generated and updated based on output events of a workflow engine of the workflow system.

11 Claims, 3 Drawing Sheets

1 South - J Smith RN Phone List

401 Wilson, Robert
- Rucker, D MD  O:215-662-5511  [Dial] [Flag]
- Wilson, Sally  H:610-231-7854  [Dial] [Flag]

402 Garcia, Maria
- ☑ Stein, B MD  P:215-662-4389  [Dial] [Flag]
- Hughes, S MD  O:215-402-9421  [Dial] [Flag]

403 Kranz, Maria
- ☑ Stein, B MD  P:215-662-4389  [Dial] [Flag]
- Kranz, John  H:514-560-7789  [Dial] [Flag]

Common Phone Numbers
- Clinical Lab  x8843  [Dial] [Flag]
- Pharmacy  x4539  [Dial] [Flag]
- Radiology  x7025  [Dial] [Flag]

Fig. 3

SYSTEM AND METHOD FOR MANAGING HEALTHCARE COMMUNICATION

CROSS-REFERENCE TO RELATED APPLICATION

This application claims priority OF U.S. Provisional Application Ser. No. 60/344,127, by D. Rucker filed on Dec. 28, 2001.

TECHNICAL FIELD OF THE INVENTION

The present invention relates generally to a system and method for managing healthcare communication and, in particular, to a system and method for dynamically generating and updating lists of patient-specific contact information that are readily accessible by healthcare providers while treating patients.

BACKGROUND

One of the most time consuming tasks in acute patient care is the coordination of care and communication between healthcare providers while providing services to multiple patients. Such communication and coordination is typically performed through telephonic communication, which provides significant delay in coordinating healthcare services. This delay is caused, in part, by the need to interrupt workflow and find relevant contact information for healthcare providers. Indeed, one may walk into any busy hospital unit, emergency room or intensive care unit, for example, and see multiple clinicians simultaneously on the telephone. The clinicians who take care of multiple patients simultaneously must make frequent phone calls to coordinate care and schedule resources such as studies, medications, treatments, and transfers. Unfortunately, these clinicians need to interrupt care, so that they could locate a chart, paper phone list, etc, or otherwise manually lookup phone numbers or other contact information that they have not memorized.

Another cause of delay in coordinating healthcare services results from having to make repeated phone calls when necessary healthcare providers are not available. Indeed, many doctors are contacted via pagers, and consequently, such doctors may or may not return the call or even be available. For example, a nurse paging a doctor may have to wait until the doctor finishes treating another patient or traveling between care facilities before the doctor returns the call. Unfortunately, every time a nurse, doctor or clinician has to interrupt his or her workflow to retrieve a phone number or make a repeated call results in both a time cost and an additional productivity loss for the task being interrupted.

Another problem associated with communication between healthcare providers is the need to track unanswered calls that need to be repeated. The task of remembering whom to call again and when to do so is especially difficult for a healthcare provider who is simultaneously taking care of several patients. The task of manually tracking calls that need to be repeated is typically the most significant source of interruption, error and delay in providing efficient patient care. Indeed, because potentially dozens of other patient assessment, care and communication tasks are being performed at the same time, a healthcare provider may forget to repeat a previous unanswered call until he/she is reminded. Moreover, for patients with certain conditions, multiple calls have to be made repetitively (e.g., for a heart attack patient, recalling the cath lab, the interventional cardiologist, the pharmacist, the attending physician of record) and it is easy to forget to make one or more of these calls. Each failure to call back in a timely fashion adds its own delay to the process of care. Paradoxically, the sicker the patient is and the more care required, the more likely it is that repeat phone calls will be needed and the more likely it is that these phone calls will be forgotten or delayed.

Typically, in a clinical care environment, healthcare providers will either rely on their memory for commonly called phone numbers or rely on phone directories, ubiquitous paper lists, and/or scribbled phone numbers to obtain necessary contact information. For patient specific phone numbers (such as those of the patient's physicians or responsible family members), such information is typically accessed from either a chart that has to be located or a demographic section of an HIS that has to be manually accessed.

Accordingly, there is a need for an automated system and method for managing healthcare communication that would minimize the delay and disruption in providing health services as described above.

SUMMARY OF THE INVENTION

The present invention is directed to a system and method for managing healthcare communication. In general, a system and method according to the present invention comprises a tool, which is integrated with a clinical information system, for dynamically generating and updating lists of patient-specific and provider-specific contact information that are readily accessible by healthcare providers while treating patients.

The tool is preferably integrated with a call management system for tracking and flagging clinically necessary telephone calls, for example, that need to be repeated. The tool preferably supports IP (Internet Protocol) telephony that allows the call to be made directly by selecting a phone number to be called from a displayed list of contact information rather than manually dialing it, and flagging the call for redial if the call is unanswered.

Furthermore, the tool is preferably integrated with a workflow system to provide dynamic task assignment wherein the lists of contact information are dynamically generated and updated based on output events of a workflow engine.

In one aspect of the present invention, a method for managing healthcare communication comprises applying predetermined criteria to search one or more sources for contact information comprising, e.g., telephone numbers of healthcare personnel, responsible family members, etc., that are associated with a particular patient. The contact information that is acquired is sorted and incorporated in a list, which is rendered and presented (e.g., displayed) to a user.

In another aspect of the present invention, a method is provided for presenting a user interface for use in healthcare related communication management. In response to a user command, a user interface generates one or more display windows comprising contact information for use in establishing communication links to personnel associated with a particular patient. One or more selectable indicators (e.g., GUI button) are provided to prompt a user to re-contact one or more specific personnel using associated contact information. For example, a user can interact with a displayed list of contact information by "flagging" calls that need to be repeated. A call can be flagged either manually or automatically upon the occurrence of a predetermined event (e.g., receiving busy signal). Preferably, the "flag" allows a user to set a priority identifier that indicates a relative importance level assigned to the re-contact prompt. Preferably, timing mechanisms are provided for determining when to display escalating alerts and reminders to call. An activated selectable indicator can be deactivated to remove a re-contact prompt in response to a command, which may be a user command or predetermined system command.

These and other objects, features and advantages of the present invention will be described or become apparent from the following detailed description of preferred embodiments, which is to be read in connection with the accompanying drawings.

BRIEF DESCRIPTION OF THE DRAWINGS

FIG. 3 is an exemplary diagram of a user interface for presenting a list of contact information according to one aspect of the present invention.

DETAILED DESCRIPTION OF PREFERRED EMBODIMENTS

The present invention is directed to a system and method for managing healthcare communication. It is to be understood that the system and methods described herein in accordance with the present invention may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

Figure 1:
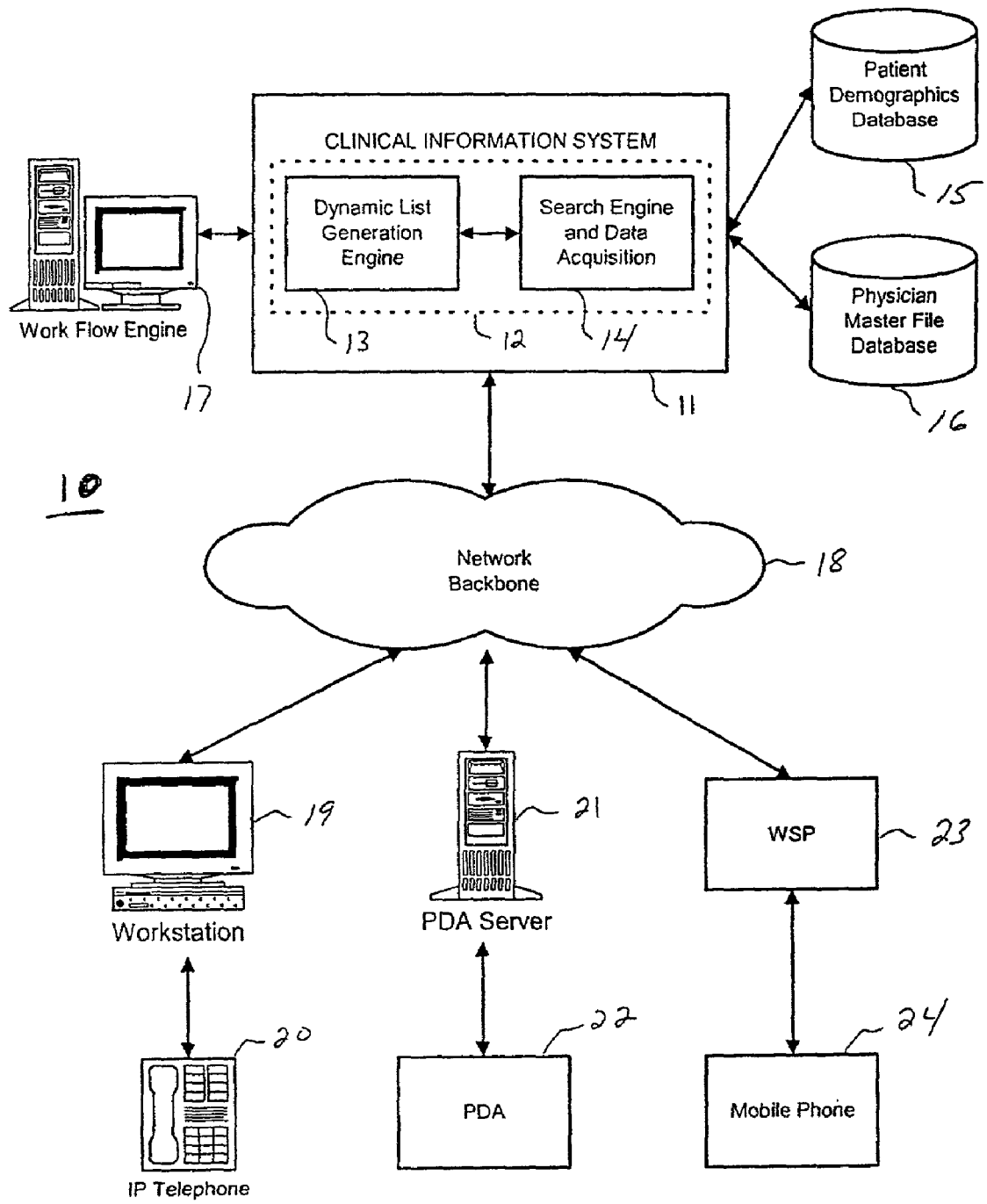
FIG. 1 is a block diagram of a system for managing healthcare communication according to an embodiment of the present invention.

Referring to FIG. 1, a block diagram illustrates a system 10 according to an embodiment of the present invention for managing communication among healthcare providers. In general, the system 10 comprises a clinical information system 11 comprising an application 12 (or tool) that dynamically acquires and analyzes contact information from one or more sources (15, 16, 17) and generates a patient-specific and provider-specific list of contact information (e.g., phone numbers) that is transmitted over a network 18 and presented (e.g., via a GUI (graphic user interface), speech interface, or a combination thereof) to a specific caregiver in a desired delivery environment (e.g., workstation 19, cellular phone 24, PDA (personal digital assistant) 22, or any other mobile device such as a portable computer, pen device, etc.)

More specifically, the application 12 comprises a dynamic list generation engine 13 and a search engine and data acquisition module 14. In response to a user query, the search engine and data acquisition module 14 searches one or more sources of patient-specific contact information and acquires such contact information relevant to the user search query. The dynamic list generation engine 13 sorts and compiles the acquired contact information in a list of contact information that is presented to the user.

The sources of contact information comprise, e.g., a patient demographics database 15 or a physician master file database 16, or any other data source associated with the information systems registration, demographics, workflow, or configuration file sections. Indeed, the data source may comprise an electronic patient record system, a repository of patient registration information, a repository of patient non-clinical information, a repository of patient clinical information, and/or a repository of configuration information.

In another embodiment of the present invention, the tool 12 supports other productivity enhancements such as dynamic workflow task assignment, wherein the data source of contact information may comprise a task schedule information system of a workflow management system 17. The workflow management system 17 may comprise any system that is employed to coordinate computer-supported human activity by monitoring the progress of work and informing people what activities they should do next. The workflow engine 17 in the underlying clinical information system can add to the dynamic phone list described above. For example, when the workflow software learns that an MRI scan ordered on the patient will be delayed, it can place the contact information (e.g., telephone number) of the MRI scanner for rescheduling on the dynamic phone list. This can be done with or without an associated text message.

In one exemplary embodiment, the list of contact information data for a particular patient may comprise the names of attending physicians of the patient, the names of responsible family members or next-of-kin, as well as their contact information (e.g., telephone numbers). In addition, the list of contact information may comprise information associated with an ongoing care process such as the names and phone numbers of physicians who have provided care via electronic orders. It is to be appreciated that the contact information data for a particular person may comprise, for example, a work telephone number, a home telephone number, a mobile phone number, a pager number, a fax number, an Email address, an Internet Telephone address, a Universal Resource Locator (URL), an Internet Protocol (IP) address, a videophone number, and any combination thereof.

A system user (e.g., physician, clinician, nurse, etc.) can login to the clinical information system 11 over the network 18 using any one of a variety of client devices. For instance, a user can login and access the clinical information system 11 via the workstation 19, the PDA device 22 (such as a Palm Pilot or pen device) via a PDA server 21, or a cellular phone 24 via a wireless service provider 23. A list of contact information that is dynamically generated and updated by the clinical information system 11 is presented on a client device of the user. Each client device is capable of presenting the contact information to the user based on the presentation modality. For instance, a GUI (graphical user interface) window on a workstation display can be used to present the contact information or the contact information can be presented as display list (on a mobile device). In addition, any other suitable interface such as a speech interface or combination speech/GUI interface can be used depending on the modality of the client device. Preferably, the contact information is presented so that a caregiver can view a list that has each active patient listed by room or bed location with several clinically relevant and patient specific phone numbers displayed next to the patient name.

The present invention provides an advantage over current methods in which caregivers have to lookup such phone numbers because they are not repetitive enough for the doctor or nurse to memorize. The system 10 provides a process for dynamically taking these patient specific phone numbers and automatically generating and updating them with a list specific to each caregiver or care team. Rather than walking to the nursing station or ER counter or calling down the hall to the unit clerk, the caregiver could just find the numbers by looking at the display of his/her computer screen, PDA or mobile phone, for example.

It is to be understood that the system 10 may be implemented using any suitable computing environment framework such as client/server, P2P (peer-to-peer) or master/slave, for example. The network 18 may comprise any suitable network configuration such as an Intranet, a LAN (local area network), WAN (wide area network), a P2P network, a global computer network (e.g., Internet), a wireless communications network, etc. Those of ordinary skill in the art can readily envision various architectures for implementing a system for dynamically providing lists of contact information based on the teachings herein and nothing herein shall be construed as a limitation of the scope of the invention.

In another embodiment of the present invention, a dynamic contact information list generation system 10 is integrated with a call management system to thereby track when clinically necessary phone calls have to be repeated and flag or place them on a "to-do" list. For example, the tool preferably supports IP (Internet Protocol) telephony that allows the call to be made directly by selecting a phone number to be called from a displayed list of contact information rather than manually dialing it, and flagging the call for redial if the call is unanswered. For example, as shown in FIG. 1, an IP telephone 20 may be used in conjunction with the workstation 19 to automatically dial phone numbers and track unanswered calls. In a further embodiment as explained below, each phone number could have a recall flag that can be selected to present a menu that allows the user to select a priority to be specified for recall choice selected.

In a further embodiment, the dynamic call list of "to-do" calls can be integrated with the output of a workflow engine and dynamic task assignment.

Figure 2:
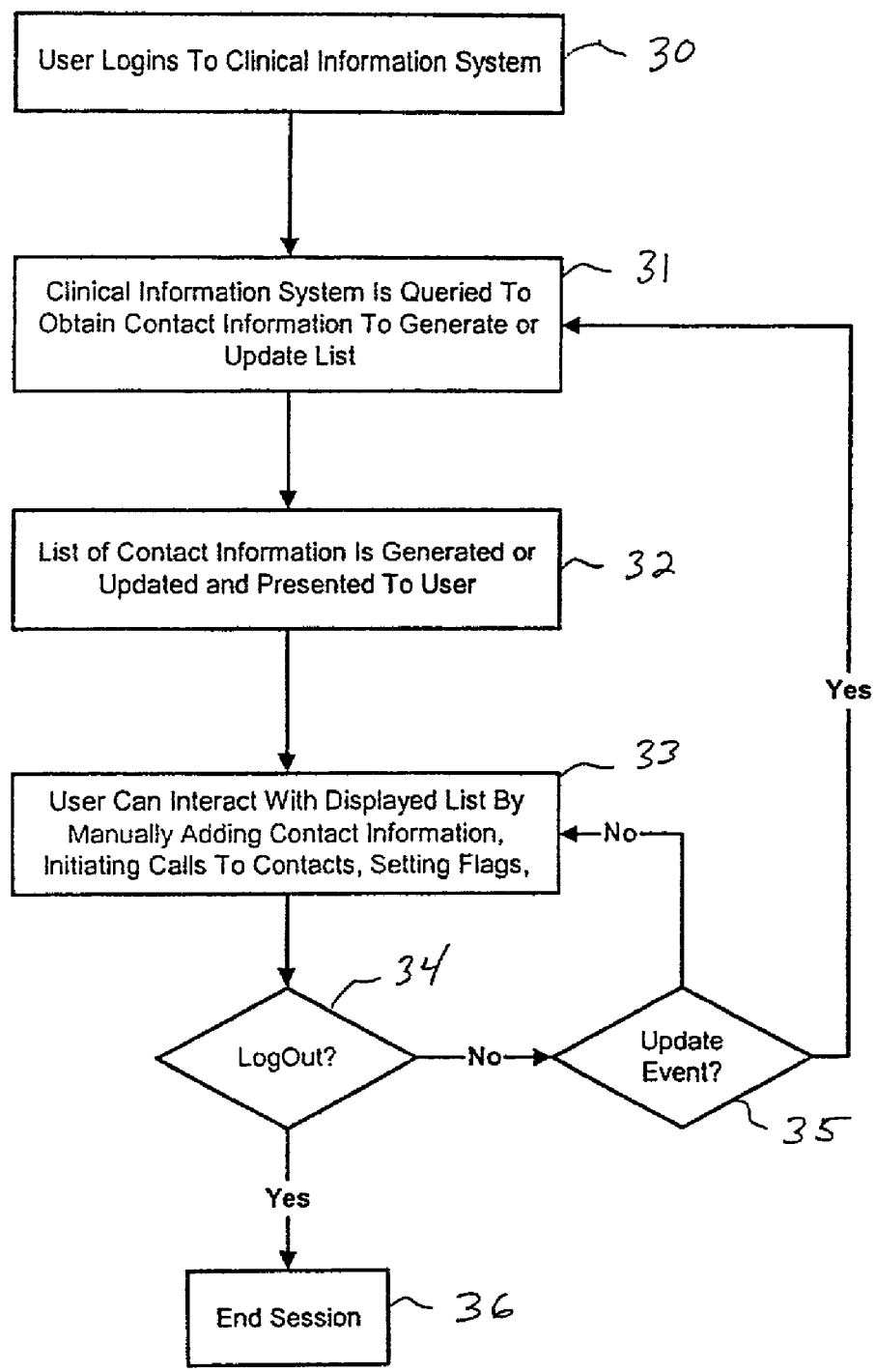
FIG. 2 is a flow diagram of a method for managing healthcare communication according to an embodiment of the present invention.

Referring now to FIG. 2, a flow diagram illustrates a method for managing healthcare communication according to an embodiment of the present invention. In particular, the method of FIG. 2 illustrates one mode of operation of the system 10 depicted in FIG. 1. Initially, a user (healthcare provider or group of healthcare providers) that wants to access the clinical information system and obtain a patient-specific list of contact information will login to the system using a desired access device (step 30). For instance, a nurse working in a nursing unit may use a workstation to access the clinical information system. It is to be understood that any suitable authentication protocol may be used for login (e.g., password, biometric identification, etc.)

Upon login, the clinical information system is queried to obtain patient-specific contact information to generate a list of contact information (step 31). For example, the clinical information system is preferably queried on a patient-by-patient basis for each patient currently known to be assigned to the user so as to provide the relevant contact information (e.g., phone numbers) and any workflow messages for the user. As noted above, one or more data sources can be accessed to obtain relevant contact information.

Using the acquired contact information, a list of contact information is dynamically created for presentation to the user (step 32). It is to be appreciated that various criteria may be applied for generating the list of contact information. For example, telephone numbers of contact persons/departments for a particular patient or group of patients may be categorized into telephone numbers that are frequently called and typically memorized by caregivers (e.g., telephone numbers for labs, radiology, admissions, ER, pharmacy, other nursing stations, etc.) and those numbers that are infrequently or intermittently called. In such case, the dynamically generated list of phone numbers may be narrowed by including only those telephone numbers that are infrequently called, although the list may include common and frequently called numbers. The computer system uses knowledge of the care provider and the patients of the care provider to dynamically generate a list of contact information. Preferably, the list of contact information comprises the patient-specific clinically relevant contact information that a caregiver will spend a significant time tracking.

Once a list of contact information is generated (step 32), the list may be presented (via the appropriate modality of the access device) either automatically or upon command by the user. FIG. 3 is a diagram of an exemplary GUI (graphic user interface) displaying a dynamically created list of telephone or pager numbers. The window display of FIG. 3 may be displayed for example on a workstation of a nurse in a nursing unit. In the exemplary embodiment of FIG. 3, a list of contact numbers for a plurality of patients of a nurse (or nursing unit) is sorted by patient name and patient location (building and room number). Each patient has one or more corresponding contact numbers of doctors, family members, etc. In the exemplary embodiment of FIG. 3, each contact number is labeled with an abbreviation such as "O" for office, "P" for pager and "H" for home. Furthermore, the exemplary list provides a list of common phone numbers for a clinical lab, pharmacy and radiology dept. The common phone numbers are numbers that are frequently called by a typical nursing unit on an inpatient hospital floor or ICU shift.

It is to be understood that FIG. 3 depicts one exemplary embodiment to illustrate principles of the invention and that those of ordinary skill in the art can readily envision other methods for presenting contact information to a user. Indeed, as explained above, the list of contact information data for a particular patient may comprise the names of attending physicians of the patient, the names of responsible family members or next-of-kin, as well as their contact information (e.g., telephone numbers). In addition, the list of contact information for a given patient may comprise, for example, contact information for each caregiver (in an ongoing treatment of a patient) who has used a computerized physician order entry system to place an order on the patient in the last 48 hours and for each caregiver who has operated on the patient during this admission). Further, the contact information data for a particular person may comprise, for example, a work telephone number, a home telephone number, a mobile phone number, a pager number, a fax number, an Email address, an Internet Telephone address, a URL, an IP address, a videophone number, and any combination thereof.

Referring back to FIG. 2, once the list of contact information is presented, the user can interact with the displayed list (step 33) in one of a variety of manners. For instance, a user can manually enter contact information for a given patient when such contact information is not presented in the generated list of contact information.

Furthermore, by issuing an appropriate command, the user can automatically initiate contact with a listed care provider using contact information in the displayed list. For instance, as shown in FIG. 3, a "dial" button is displayed for each contact person. The user can select one of the "dial" buttons (e.g., via mouse click) to automatically initiate a call to the corresponding contact person using, e.g., an IP telephone or a mobile telephone, without the user having to manually input the number or address.

Moreover, the user can interact with the displayed list by flagging calls that need to be repeated. For instance, as shown in FIG. 3, each phone number has a recall "flag" button that can be selected (via click of a mouse). If a call has to be remade, the caregiver can click on the specific phone number/contact person and set a "flag" on call again status (e.g. call in 10 minutes). The flag preferably allows the user to set a priority identifier indicating a determined relative importance level assigned to the re-contact prompt. This "flag" can be accessed with multiple UI tools such as a button or right-mouse click pull down menu. The application comprises a database to maintain flags and a timing mechanism for determining when to display escalating alerts and reminders to call.

For example, in the exemplary diagram of FIG. 3, the checked box next to the contact name "Stein. B MD" indicates that the particular doctor needs to be recontacted for the given patient. The caregiver can set one or more parameters by setting flags to repeat calls possibly with reminders and alerts, e.g., (in 10 minutes, in 30 minutes, in an hour, by the end of my shift, etc.) This can be done with a single pull mouse click. When the phone number is not on the originally generated dynamic clinical list, the care provider has the option to set a patient flag or to manually enter a phone number and then flag that phone number. Even commonly called numbers can be placed on the list (as shown in FIG. 3) for all of the call management and flagging options.

Since most errors and delays or failures to call back are based on interruptions generated by the need to care for other patients, having the patient alone flagged is likely to be able to fully remind the caregiver who needs to be called back even if the phone number to be called is not on the quick list.

The system automatically generates most of the numbers specifically needing recall as well as supporting the ability to, without any alphanumeric data entry, by just a click of a mouse, to identify those patients need this coordination of care.

It is to be appreciated that flags can be activated or deactivated manually or automatically. For instance, as explained above, a call can be manually flagged by clicking the "flag" button (FIG. 3). In addition, the user can click on a given contact name or number to flag the call.

Furthermore, using an integrated call management functionality, a call can be automatically flagged for redial upon the occurrence of one of a plurality of predetermined events such as upon receiving a busy signal or no answer when a call is placed. In this instance, the redial flag will be maintained active until the call is successful. Moreover, a flag can be automatically deactivated upon the occurrence of one of a plurality of predetermined events such as termination of communication, the expiration of a predetermined duration of communication or the detection of bi-directional communication on a link established using, e.g., the "dial" button to contact a given contact person.

In addition, the redial flag for a call can be activated or deactivated in response to communication received by the clinical information system. For instance, the received communication may be derived from a task being performed by a healthcare personnel, or automatically generated upon occurrence of a clinical related event associated with a particular patient. By way of example, workflow messages can be sent to the list on an interrupt driven basis and phone calls can be taken off the list and placed in another workflow process management tool (such as a cell phone).

Referring again to FIG. 2, as the user interacts with the system and has not logged out (negative determination in step 34) to end the session (step 36), if an update event occurs (affirmative result in step 35), the list of contact information will be updated and presented to the user (steps 31-32). For instance, in a preferred embodiment of the present invention, at the expiration of predetermined time intervals after user login, the clinical information system will be queried on a patient-by-patient basis for each patient known to be currently assigned to the user so as to update the list of contact information and provide relevant workflow messages to the user. Thus, the expiration of the predetermined time period comprises an update event.

Furthermore, as noted above, an update event may be an interrupt event wherein workflow messages are sent to a displayed list on an interrupt driven basis and phone calls can be taken off the list and placed in another workflow process management tool (such as a cell phone).

In addition, the activation and deactivation of redial flags comprises update events that result in an update of the list of contact information.

In summary, there are many advantages associated with the present invention. For instance, the present invention utilizes access devices such as computers, cell phones PDAs, etc, which are commonly used by clinicians, to present and display the contact information. The clinicians do not have to interrupt their workflow to travel to the nursing station, unit clerk, or chart to obtain desired contact information.

Further, the invention enables patient and provider specific phone numbers to be integrated into a current workflow process. In addition, the list of contact information for patients of a care provider is dynamically generated and updated and a continuing basis. Further, the list of contact information comprises various patient-specific clinically relevant numbers that a caregiver typically will need to track when caring for a patient. Moreover, the present invention provides an integrated system for managing call communication and redial as part of the same interface and workflow. Practical flagging of phone numbers needing recall is provided without requiring alphanumeric data entry. Flags for redial can be set either manually or automatically based on the occurrence of one or more predetermined events.

Furthermore, the present invention directly addresses the major acute productivity gap that currently exists in care communication and coordination and directly addresses interruption driven errors by providing a workflow integrated set of flags for caregivers to remember desired sets of tasks. The tool can communicate with workflow engines and handle inbound and outbound workflow and task management messages.

The present invention is extensible to other related fields. Indeed, the dynamic generation of contact lists and call tracking is applicable to a variety of hardware software combinations such as cell phones and PDAS. At the heart of the system is support for the interrupt-driven workflow with unpredictable clinical needs for phone calls and recalling. This may extend to other interrupt driven workflows where call management is based in part on predictable tasks and in part on unpredictable tasks using the nature of the predictable tasks (who the patient is, who the provider is) to help with the somewhat unpredictable tasks (whom might I need to call, whom would I need to be reminded to call again).

Although illustrative embodiments have been described herein with reference to the accompanying drawings, it is to be understood that the present invention is not limited to those precise embodiments, and that various other changes and modifications may be affected therein by one skilled in the art without departing from the scope of the invention.

What is claimed is:

1. A method for managing healthcare communication, comprising the steps of:

applying predetermined search criteria in searching a plurality of sources including a clinical information system for contact information comprising telephone contact data for use in establishing communication links to personnel and patients associated with a particular healthcare worker;

automatically and intermittently acquiring and sorting the contact information;

automatically and intermittently acquiring workflow messages provided by a workflow management system for monitoring the progress of work and informing personnel of tasks to be performed, in response to a clinical event associated with a particular patient;

incorporating the acquired and sorted contact information together with telephone contact status information in data representative of a list of contact information for said particular healthcare worker; and initiating generation of a display image using said data representative of said list of contact information for said particular healthcare worker, said display image indicating workflow messages generated by said workflow management system identifying tasks associated with said particular patient and assigned to said particular healthcare worker and telephone contact status and initiating direct voice communication with said personnel, informing said personnel of said tasks to perform identified by said workflow messages using said acquired and sorted contact information, in response to selection by said particular healthcare worker of an image element in said display image.

2. A method according to claim 1, including the steps of, incorporating data indicating a work task of said particular healthcare worker in said display image and indicating a worker associated with said work task to be contacted; and wherein said telephone contact status enables initiation of communication with personnel supporting performance of tasks in at least one of, (a) a laboratory department, (b) a radiology department, (c) a pharmacy, (d) a nurses station, (e) admissions and (f) and emergency room, said workflow messages are automatically generated in response to a clinical event and said plurality of sources comprises at least one of (a) an electronic patient record system, (b) a repository of patient registration information, (c) a repository of patient non-clinical information, (d) a repository of patient clinical information, (e) a task schedule information system, and (f) a configuration information repository.

3. A method according to claim 1, including the step of employing a workflow management system in dynamically adding tasks to a list of tasks of said particular healthcare worker wherein said particular healthcare worker comprises at least one of (a) an individual involved in healthcare delivery and (b) a group of individuals involved in healthcare delivery and said display image presents a prioritized list of entities to be contacted using the contact information.

4. A method according to claim 1, wherein said display image enables initiation of communication with a worker associated with a workflow message using said acquired and sorted contact information and in applying said predetermined search criteria, said plurality of sources is searched for contact data of one or more of (a) an attending physician of the patient, (b) a physician involved in an order of an item for the particular patient, (c) a family member, and (d) next of kin.

5. A method according to claim 1, wherein said workflow messages are acquired from a clinical information system and the contact information comprises at least one of (a) a work telephone number, (b) a home telephone number, (c) a mobile phone number, (d) a pager number, (e) a fax number, (f) an Email address, (g) an Internet Telephone address, (h) a Universal Resource Locator (URL), (i) an Internet Protocol (IP) address, and (j) a videophone number.

6. A method according to claim 1, further comprising the step of using contact information from the list of contact information in establishing a communication link with a selected one of the personnel via at least one of, (a) a telephone network, (b) the Internet, (c) a Local Area Network, (d) a Wide Area Network (WAN) and (e) a pager network.

7. A method according to claim 1, wherein said contact status comprises a selectable indicator for prompting a user to re-contact one of the personnel using particular contact data of the contact information.

8. A program storage device readable by a machine, tangibly embodying a program of instructions executable by the machine to perform method steps for managing healthcare communication, the method steps comprising:

applying predetermined search criteria in searching a plurality of sources including a clinical information system for contact information comprising telephone contact data for use in establishing communication links to personnel and patients associated with a particular healthcare worker;

automatically and intermittently acquiring and sorting the contact information;

automatically and intermittently acquiring workflow messages generated by a workflow management system for monitoring the progress of work and informing personnel of tasks to be performed in response to a clinical event associated with a particular patient;

incorporating the acquired and sorted contact information together with telephone contact status information in data representative of a list of contact information for said particular healthcare worker; and initiating generation of a display image using said data representative of said list of contact information for said particular healthcare worker, said display image indicating workflow messages generated by said workflow management system identifying tasks associated with said particular patient and assigned to said particular healthcare worker and telephone contact status and initiating direct voice communication with said personnel, informing said personnel of said tasks to perform identified by said workflow messages using said acquired and sorted contact information, in response to selection by said particular healthcare worker of an image element in said display image.

9. A method according to claim 1, wherein said telephone contact status data indicates a success of said initiated communication and further comprising the step of:

in response to said telephone contact status data indicating an unsuccessful communication, automatically re-initiating said communication using said acquired and sorted contact information at a predetermined time interval.

10. A method according to claim 1, further comprising the steps of:

in response to a non-completed communication,
automatically flagging said non-completed communication with data indicating said communication needs to be repeated at a predetermined time interval,
automatically tracking said flagged communication data; and
at least one of (a) displaying an alert indicative of said predetermined time interval; and (b) automatically re-initiating said non-completed communication using said acquired and sorted contact information.

11. A system for managing healthcare workflow and communication, comprising:

a workflow engine for monitoring the progress of work and informing personnel of tasks to be performed and for automatically and intermittently providing workflow messages generated in response to a clinical event associated with a particular patient;

a clinical information system for,
applying predetermined search criteria in searching a plurality of sources including a clinical information system for contact information comprising telephone contact data for use in establishing communication links to personnel and patients associated with a particular healthcare worker;
automatically and intermittently acquiring and sorting the contact information;
incorporating the acquired and sorted contact information together with telephone contact status information in data representative of a list of contact information for said particular healthcare worker; and a user interface device for initiating generation of a display image using said data representative of said list of contact information for said particular healthcare worker, said display image indicating workflow messages provided by said workflow management system identifying tasks associated with said particular patient and assigned to said particular healthcare worker and telephone contact status and initiating direct voice communication with said personnel, informing said personnel of said tasks to perform identified by said workflow messages using said acquired and sorted contact information, in response to selection by said particular healthcare worker of an image element in said display image.

\* \* \* \* \*